United States Patent [19]
Thornton

[11] Patent Number: 5,954,048
[45] Date of Patent: *Sep. 21, 1999

[54] DEVICE AND METHOD FOR IMPROVING BREATHING

[76] Inventor: W. Keith Thornton, 5524 Edlen, Dallas, Tex. 75220

[ * ] Notice: This patent is subject to a terminal disclaimer.

[21] Appl. No.: 08/837,418

[22] Filed: Apr. 16, 1997

Related U.S. Application Data

[63] Continuation-in-part of application No. 08/582,526, Jan. 3, 1996, abandoned, which is a continuation-in-part of application No. 08/253,949, Jun. 3, 1994, Pat. No. 5,537,994.

[51] Int. Cl.⁶ .................................................. A61M 21/00
[52] U.S. Cl. .............................. 128/201.18; 128/201.26; 128/204.18; 128/848
[58] Field of Search ......................... 128/204.18, 201.18, 128/201.26, 206.29, 200.24, 848, 859, 861, 862, 869

[56] References Cited

U.S. PATENT DOCUMENTS

| Re. 33,442 | 11/1990 | George ..................................... 128/860 |
| 746,869 | 12/1903 | Moulton . |
| 774,446 | 11/1904 | Moulton . |
| 885,196 | 4/1908 | Steil . |
| 893,213 | 7/1908 | Whiteway . |

(List continued on next page.)

FOREIGN PATENT DOCUMENTS

| 0312368 | 4/1989 | European Pat. Off. . |
| 0359135 | 3/1990 | European Pat. Off. . |
| 156627 | 12/1904 | Germany . |
| 2320501 | 11/1974 | Germany . |
| 3543931A | 6/1987 | Germany . |
| 3707952 | 9/1988 | Germany . |
| 3719009A | 12/1988 | Germany . |
| 1569129 | 6/1980 | United Kingdom . |

OTHER PUBLICATIONS

Supplementary European Search Report, mailed Mar. 23, 1998.
*Mayo Clinic Health Letter*, vol. 13, No. 7, "Snoring," Jul. 1995.
Photocopies of 2–piece dental device manufactured by Currie–Gibson Dental Laboratory, Inc. prior to Apr. 13, 1993.
Farrar & McCarty, "A Clinical Outline of Temporomandibular Joint Diagnosis and Treatment," Normandie Study Group for TMJ Dysfunction, 1993, 3 pages.
Professional Positioners brochure "Dedicated to excellence", 4 pages (date unknown).
Great Lakes Orthodontics, Ltd., "Nocturnal Airway Patency Appliance™ (NAPA)," General Instructions, undated, 2 pages.
Schmidt–Nowara, et al., "Oral Appliances for Treatment of Snoring and Obstructive Sleep Apnea: A Review," *Sleep*, 18(6):501–51, 1995.
George, "Treatment of Snoring and Obstsructive Sleep Apnea with a Dental Device," *General Denistry*, Jul.–Aug. 1993, 5 pages.

*Primary Examiner*—John G. Weiss
*Assistant Examiner*—V. Srivastava
*Attorney, Agent, or Firm*—Baker & Botts, L.L.P.

[57] ABSTRACT

A device (10) for improving the breathing of a user includes an upper arch (12) adapted to receive at least some of the user's upper teeth and a lower arch (14) adapted to receive at least some of the user's lower teeth. A hook (104) is coupled to the upper arch (12) and is uncoupled from the lower arch (14) until the device (10) is inserted into the user's mouth. The hook (104) removably engages the lower arch (14) after the device (10) has been inserted into the user's mouth to adjustably position the lower arch (14) forwardly relative to the upper arch (14). At least a portion (102) of an adjustor (100) associated with the upper arch (12) may rotate to adjust the hook (104) forwardly relative to the upper arch (12).

20 Claims, 7 Drawing Sheets

U.S. PATENT DOCUMENTS

| | | | |
|---|---|---|---|
| 1,076,534 | 10/1913 | Wallen . | |
| 1,146,264 | 7/1915 | Kelly . | |
| 1,483,694 | 2/1924 | Stukey . | |
| 1,649,664 | 11/1927 | Carter . | |
| 1,674,336 | 6/1928 | King . | |
| 2,171,695 | 9/1939 | Harper . | |
| 2,178,128 | 10/1939 | Waite | 128/136 |
| 2,383,649 | 8/1945 | Heidbrink | 128/142 |
| 2,424,533 | 7/1947 | Faires | 128/136 |
| 2,521,039 | 9/1950 | Carpenter | 128/136 |
| 2,521,084 | 9/1950 | Oberto | 128/141 |
| 2,531,222 | 11/1950 | Kesling | 32/14 |
| 2,574,623 | 11/1951 | Clyde | 128/136 |
| 2,590,118 | 3/1952 | Oddo, Jr. | 128/136 |
| 2,627,268 | 2/1953 | Leppich | 128/136 |
| 2,833,278 | 5/1958 | Ross | 128/136 |
| 2,867,212 | 1/1959 | Nunn, Jr. | 128/136 |
| 2,882,893 | 4/1959 | Godfroy | 128/136 |
| 3,107,668 | 10/1963 | Thompson | 128/136 |
| 3,124,129 | 3/1964 | Grossberg | 128/136 |
| 3,132,647 | 5/1964 | Corniello | 128/136 |
| 3,219,033 | 11/1965 | Wallshein | 128/136 |
| 3,277,892 | 10/1966 | Tepper | 128/172.1 |
| 3,312,216 | 4/1967 | Wallshein | 128/136 |
| 3,321,832 | 5/1967 | Weisberg | 32/32 |
| 3,434,470 | 3/1969 | Strickland | 128/136 |
| 3,457,916 | 7/1969 | Wolicki | 128/136 |
| 3,513,838 | 5/1970 | Foderick et al. | 128/861 |
| 3,522,805 | 8/1970 | Wallshein | 128/136 |
| 3,854,208 | 12/1974 | Arant | 32/19 |
| 3,864,832 | 2/1975 | Carlson et al. | 128/136 |
| 3,871,370 | 3/1975 | McDonald | 128/136 |
| 3,884,226 | 5/1975 | Tepper | 128/136 |
| 4,016,650 | 4/1977 | Leusner et al. | 32/17 |
| 4,026,024 | 5/1977 | Tradowsky | 32/19 |
| 4,114,614 | 9/1978 | Kesling | 128/136 |
| 4,169,473 | 10/1979 | Samelson | 128/136 |
| 4,182,312 | 1/1980 | Mushabac | 433/68 |
| 4,227,877 | 10/1980 | Tureaud et al. | 433/37 |
| 4,289,127 | 9/1981 | Nelson | 128/207.14 |
| 4,304,227 | 12/1981 | Samelson | 128/136 |
| 4,376,628 | 3/1983 | Aardse | 433/80 |
| 4,382,783 | 5/1983 | Rosenberg | 433/19 |
| 4,433,956 | 2/1984 | Witzig | 433/7 |
| 4,439,147 | 3/1984 | Magill et al. | 433/3 |
| 4,439,149 | 3/1984 | Devincenzo | 433/6 |
| 4,470,413 | 9/1984 | Warncke | 128/201.18 |
| 4,495,945 | 1/1985 | Leigner | 128/200.26 |
| 4,505,672 | 3/1985 | Kurz | 433/6 |
| 4,553,549 | 11/1985 | Pope et al. | 128/421 |
| 4,568,280 | 2/1986 | Ahlin | 433/6 |
| 4,569,342 | 2/1986 | von Nostitz | 128/136 |
| 4,593,686 | 6/1986 | Lloyd et al. | 128/136 |
| 4,602,905 | 7/1986 | O'Keefe, III | 433/41 |
| 4,639,220 | 1/1987 | Nara et al. | 433/69 |
| 4,655,213 | 4/1987 | Rapoport et al. | 128/205.25 |
| 4,669,459 | 6/1987 | Spiewak et al. | 128/136 |
| 4,676,240 | 6/1987 | Gardy | 128/207.14 |
| 4,715,368 | 12/1987 | George | 128/136 |
| 4,773,853 | 9/1988 | Kussick | 433/6 |
| 4,799,500 | 1/1989 | Newburg | 128/859 |
| 4,862,903 | 9/1989 | Campbell | 128/861 |
| 4,901,737 | 2/1990 | Toone | 128/848 |
| 4,919,128 | 4/1990 | Kopala et al. | 128/207.18 |
| 4,932,867 | 6/1990 | Ueno | 433/69 |
| 4,955,393 | 9/1990 | Adell | 128/859 |
| 5,003,994 | 4/1991 | Cook | 128/848 |
| 5,018,533 | 5/1991 | Hawkins | 128/848 |
| 5,028,232 | 7/1991 | Snow | 433/24 |
| 5,042,506 | 8/1991 | Liberati | 128/848 |
| 5,046,512 | 9/1991 | Murchie | 128/848 |
| 5,052,409 | 10/1991 | Tepper | 128/859 |
| 5,056,534 | 10/1991 | Wright | 128/848 |
| 5,078,600 | 1/1992 | Austin | 433/73 |
| 5,092,346 | 3/1992 | Hays et al. | 128/848 |
| 5,103,838 | 4/1992 | Yousif | 128/859 |
| 5,117,816 | 6/1992 | Shapiro et al. | 128/200.24 |
| 5,154,184 | 10/1992 | Alvarez | 128/848 |
| 5,154,609 | 10/1992 | George | 433/68 |
| 5,183,057 | 2/1993 | Syrop et al. | 128/845 |
| 5,188,529 | 2/1993 | Luth | 433/68 |
| 5,267,862 | 12/1993 | Parker | 433/215 |
| 5,277,202 | 1/1994 | Hays | 128/848 |
| 5,284,161 | 2/1994 | Karell | 128/848 |
| 5,313,960 | 5/1994 | Tomasi | 128/848 |
| 5,316,020 | 5/1994 | Truffer | 128/848 |
| 5,365,945 | 11/1994 | Halstrom | 128/848 |
| 5,373,859 | 12/1994 | Forney | 128/846 |
| 5,409,017 | 4/1995 | Lowe | 128/848 |
| 5,427,117 | 6/1995 | Thornton | 128/848 |
| 5,537,994 | 7/1996 | Thornton | 128/204.18 |
| 5,566,683 | 10/1996 | Thronton | 128/848 |
| 5,755,219 | 5/1998 | Thornton | 128/201.18 |

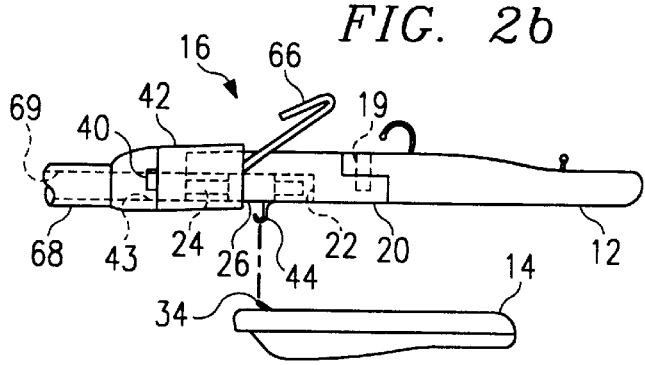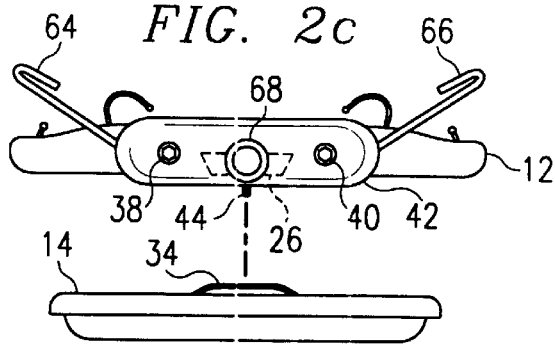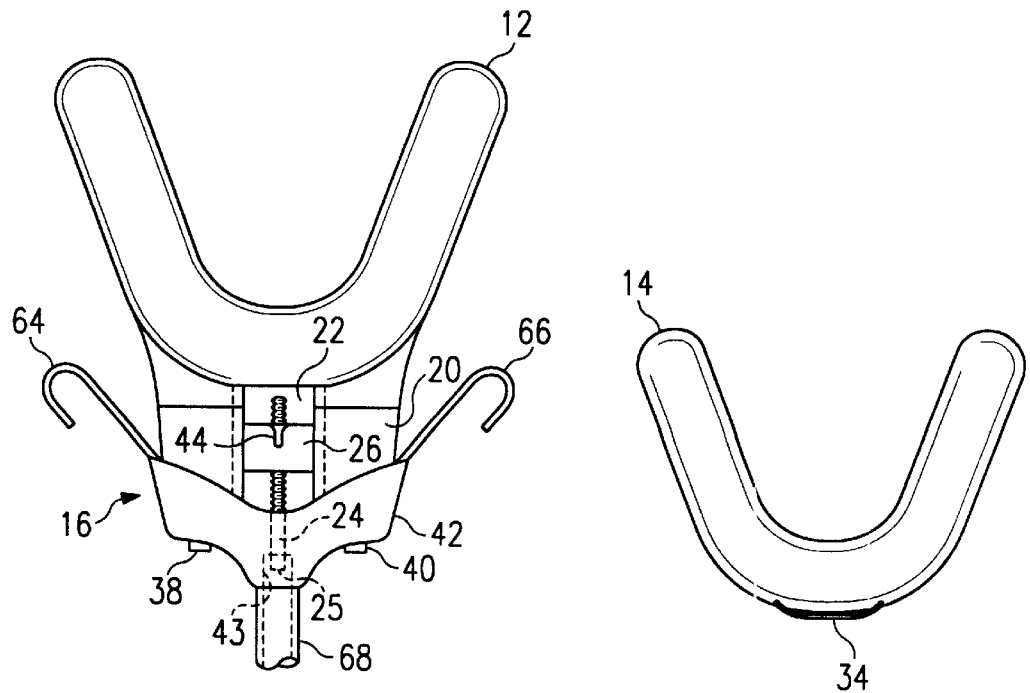

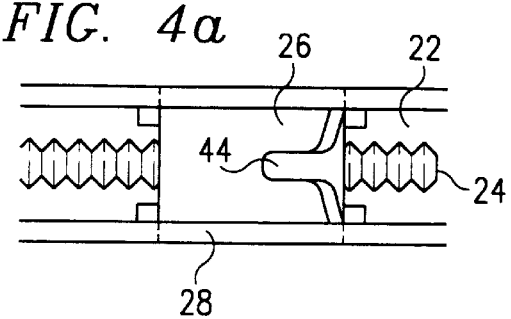
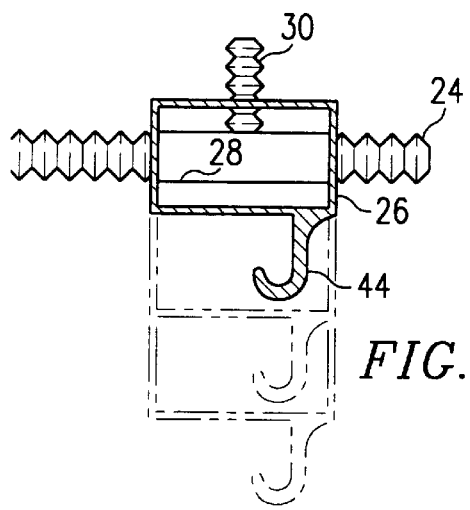
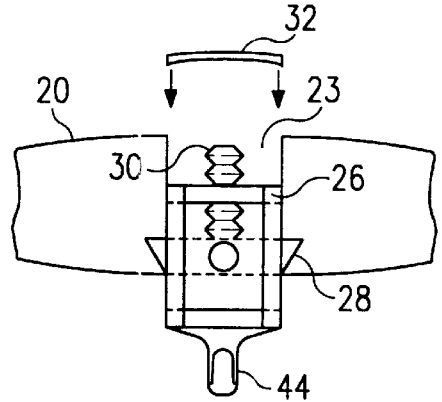
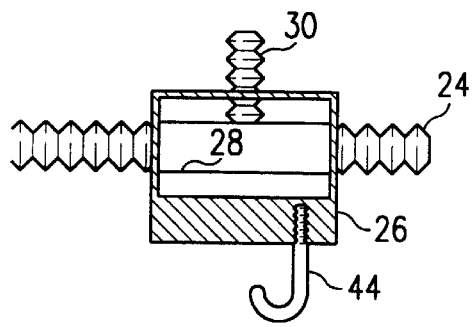
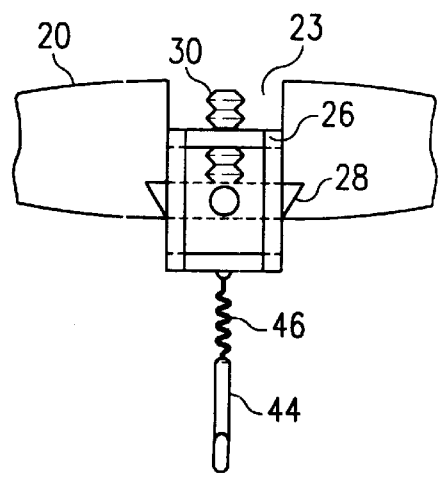
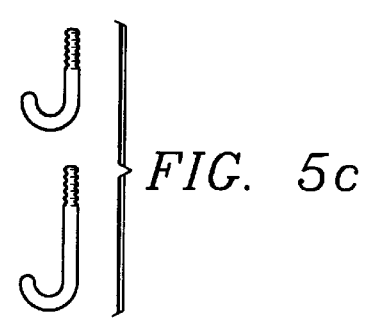

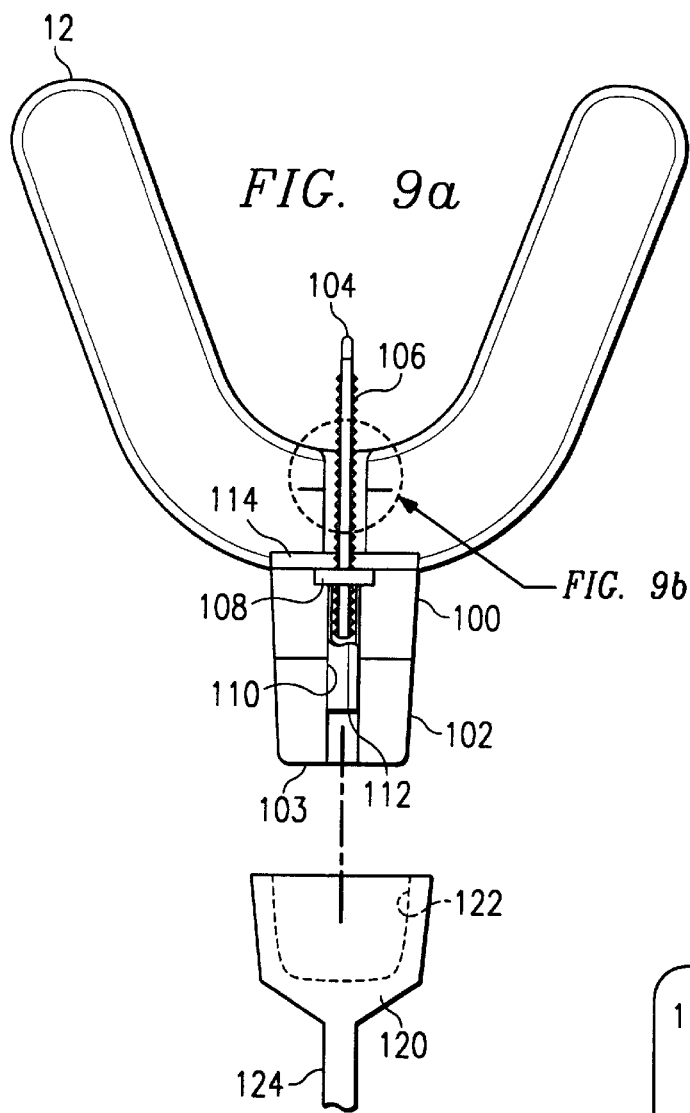
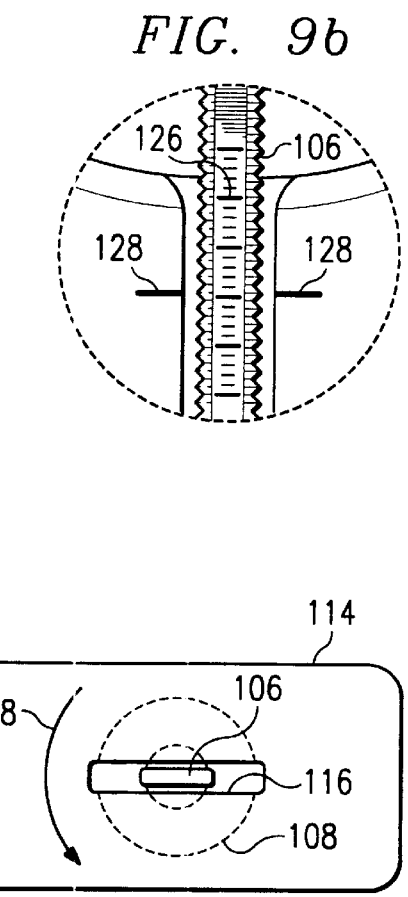
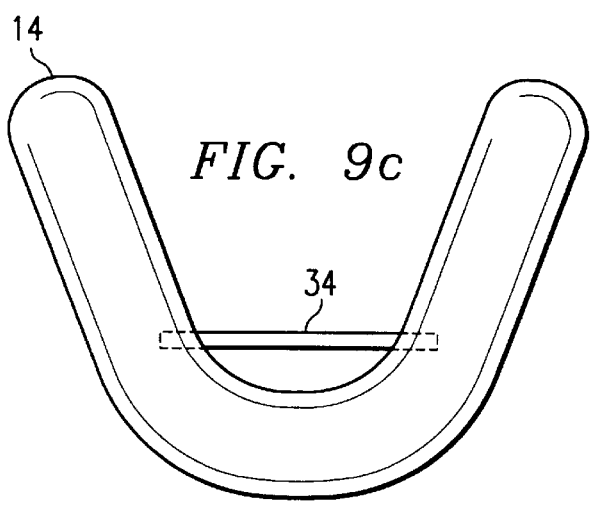

DEVICE AND METHOD FOR IMPROVING BREATHING

CROSS-REFERENCE TO RELATED APPLICATIONS

This application is a continuation-in-part of U.S. application Ser. No. 08/582,526, filed Jan. 3, 1996, by W. Keith Thornton and entitled "Device for Improving Breathing," abandoned, which is a continuation-in-part of U.S. application Ser. No. 08/253,949, filed Jun. 3, 1994, by W. Keith Thornton and entitled "Combination Face Mask and Dental Device for Improved Breathing During Sleep," now U.S. Pat. No. 5,537,994.

This application is also related to U.S. application Ser. No. 08/594,904, filed Jan. 31, 1996, by W. Keith Thornton and entitled "Device for Improving Breathing," pending, which is a continuation of U.S. application Ser. No. 08/253,949, filed Jun. 3, 1994, by W. Keith Thornton and entitled "Combination Face Mask and Dental Device for Improved Breathing During Sleep," now U.S. Pat. No. 5,537,994. This application is also related to U.S. application Ser. No. 08,645,673, filed May 14, 1996, by W. Keith Thornton and entitled "Device for Improving Breathing," pending, which is a continuation-in-part of U.S. application Ser. No. 08/253, 949, filed Jun. 3, 1994, by W. Keith Thornton and entitled "Combination Face Mask and Dental Device for Improved Breathing During Sleep," now U.S. Pat. No. 5,537,994.

This application is further related to U.S. application Ser. No. 08/828,523, filed Mar. 31, 1997, by W. Keith Thornton and entitled "Apparatus for Prevention of Snoring and Improved Breathing During Sleep," pending, which is a file wrapper continuation of U.S. application Ser. No. 08/363, 639, filed Dec. 24, 1994, by W. Keith Thornton and entitled "Apparatus for Prevention of Snoring and Improved Breathing During Sleep," now abandoned, which is a continuation of U.S. application Ser. No. 08/129,598, filed Sep. 29, 1993, by W. Keith Thornton and entitled "Apparatus for Prevention of Snoring and Improved Breathing During Sleep," now U.S. Pat. No. 5,427,117. This application is further related to U.S. application Ser. No. 08/410,325, filed Mar. 24, 1995, by W. Keith Thornton and entitled "Apparatus for Prevention of Snoring and Improved Breathing During Sleep," now U.S. Pat. No. 5,566,683, which is a continuation-in-part of U.S. application Ser. No. 08/129,598, filed Sep. 29, 1993, by W. Keith Thornton and entitled "Apparatus for Prevention of Snoring and Improved Breathing During Sleep," now U.S. Pat. No. 5,427,117.

This application is additionally related to U.S. application Ser. No. 08/787,529, filed Jan. 21, 1997, by W. Keith Thornton and entitled "Method and Apparatus for Adjusting a Dental Device," pending, which is a file wrapper continuation of U.S. application Ser. No. 08/435,277, filed May 5, 1995, by W. Keith Thornton and Andrew O. Jamieson and entitled "Method and Apparatus for Adjusting a Dental Device," now abandoned, which is a file wrapper continuation of U.S. application Ser. No. 08/218,719, filed Mar. 24, 1994, by W. Keith Thornton and Andrew O. Jamieson and entitled "Method and Apparatus for Adjusting a Dental Device," now abandoned. This application is additionally related to U.S. application Ser. No. 08/501,437, filed Sep. 18, 1995, by W. Keith Thornton and Andrew O. Jamieson and entitled "Apparatus for Adjusting a Dental Device," now U.S. Pat. No. 5,678,567, which is a continuation of U.S. application Ser. No. 08/435,277, filed May 5, 1995, by W. Keith Thornton and Andrew O. Jamieson and entitled "Method and Apparatus for Adjusting a Dental Device," now abandoned, which is a file wrapper continuation of U.S. application Ser. No. 08/218,719, filed Mar. 24, 1994, by W. Keith Thornton and Andrew O. Jamieson and entitled "Method and Apparatus for Adjusting a Dental Device," now abandoned.

TECHNICAL FIELD OF THE INVENTION

This invention relates generally to oral appliances, and more particularly to a device and method for improving the breathing of a user.

BACKGROUND OF THE INVENTION

Many people experience breathing problems, which may result in difficulty sleeping, in snoring, or in other more serious conditions such as obstructive sleep apnea. One treatment for such breathing disorders involves the use of devices inserted into a user's mouth for extending the user's lower jaw forward. These devices open the breathing passageway more fully to allow easier breathing through the nose and mouth.

As technology advances and users continue to demand increased performance and comfort, improving the breathing of users becomes increasingly important. Previous devices for improving breathing include upper and lower arches that are connected together outside a user's mouth and then inserted into the user's mouth as an integrated unit to position the user's lower jaw forward. Although these devices may treat some breathing problems, these devices do not sufficiently treat more serious conditions such as obstructive sleep apnea while allowing the user or a clinical professional to adjust the position of the user's lower jaw relatively easily after the arches have been inserted into the user's mouth. Moreover, these devices are often unwieldy and uncomfortable for the user with respect to insertion into the user's mouth and subsequent use after insertion into the user's mouth. As a result of these and other deficiencies, previous devices and methods for improving breathing are inadequate for the needs of many users.

SUMMARY OF THE INVENTION

The device and method of the present invention reduce or eliminate disadvantages and problems associated with devices and methods for improving breathing.

In one embodiment of the present invention, a device for improving the breathing of a user includes an upper arch adapted to receive at least some of the user's upper teeth and a lower arch adapted to receive at least some of the user's lower teeth. A hook is coupled to the upper arch and is uncoupled from the lower arch until the device is inserted into the user's mouth. The hook removably engages the lower arch after the device has been inserted into the user's mouth to adjustably position the lower arch forwardly relative to the upper arch. An adjustor that is associated with the upper arch may rotate to adjust the hook forwardly relative to the upper arch.

Important technical advantages of the device and method of the present invention include providing an upper arch having a hook that removably engages a lower arch to adjustably position the lower arch, and thus the user's lower jaw, forwardly relative to the upper arch. Another important technical advantage includes allowing the lower arch to be adjustably positioned forwardly while allowing the lower jaw to move laterally. The present invention increases the opening of the user's breathing passageway to increase effectiveness of treatments for breathing disorders such as obstructive sleep apnea, while remaining more comfortable for the user. The upper and lower arches may also include a deformable material that allows the device to be customized by the user as well as by a clinical professional, decreasing the cost of providing the device to the user. Yet another important technical advantage of the present invention includes providing a removable connector for coupling the device to a face mask that may be used in cooperation with the device and a gas supply system for treatment of snoring, obstructive sleep apnea, or other breathing disorders.

BRIEF DESCRIPTION OF THE DRAWINGS

For a more complete understanding of the present invention and its advantages, reference is now made to the following descriptions taken in conjunction with the accompanying drawings, in which like reference numbers indicate like features and wherein:

FIGS. 2a through 2d illustrate various views of a device for improving breathing;

FIGS. 4a through 4c illustrate a hooking element;

FIGS. 5a through 5d illustrate another alternative device for improving breathing;

FIGS. 9a through 9c illustrate upper and lower arches of an exemplary device for improving breathing according to the present invention; and FIG. 10 illustrates a front wall having a slot for a hook according to the present invention.

DETAILED DESCRIPTION OF THE INVENTION

Figure 1A:
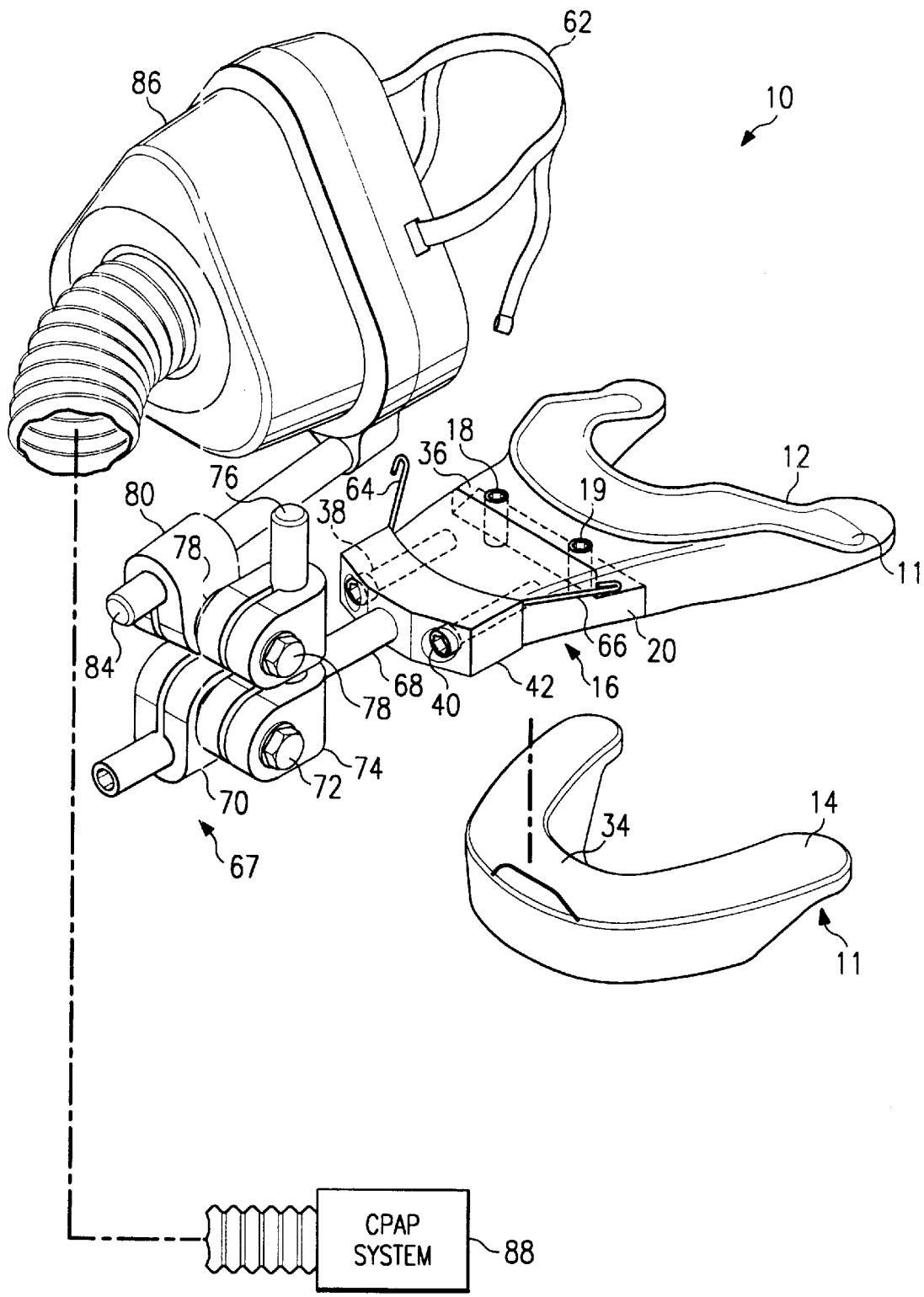
FIGS. 1a and 1b illustrate a device for improving the breathing of a user.

FIG. 1a illustrates a device for improving breathing that includes an upper arch 12 adapted to receive at least some of a user's upper teeth and a lower arch 14 adapted to receive at least some of the user's lower teeth. Upper arch 12 and lower arch 14 are each adapted to receive a deformable material 11 in which molds of at least some of the user's upper and lower teeth, respectively, may be formed. Deformable material 11 may be the ethylene-vinyl acetate copolymer resin sold under the name ELVAX or any other deformable material suitable for forming molds of a user's teeth, for example, an appropriate polycaprolactone polymer. In one embodiment, deformable material 11 may be heated to approximately 150° F. or another suitable temperature so as to place deformable material 11 in its deformable state. Upper arch 12 and lower arch 14 are then inserted into the user's mouth, separately or together, and the user bites down to deform deformable material 11 into the shape of at least some of the user's teeth. Upper arch 12 and lower arch 14 are removed from the user's mouth and allowed to cool and harden. Arches 12 and 14 of device 10 may be customized in this manner by the user or a clinical professional.

Figure 1B:
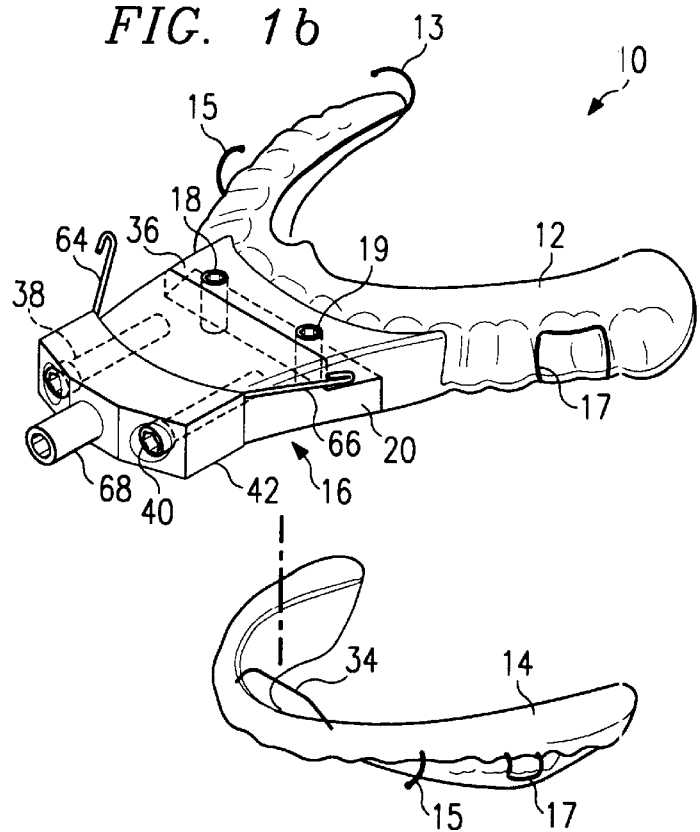
Figure 2A:
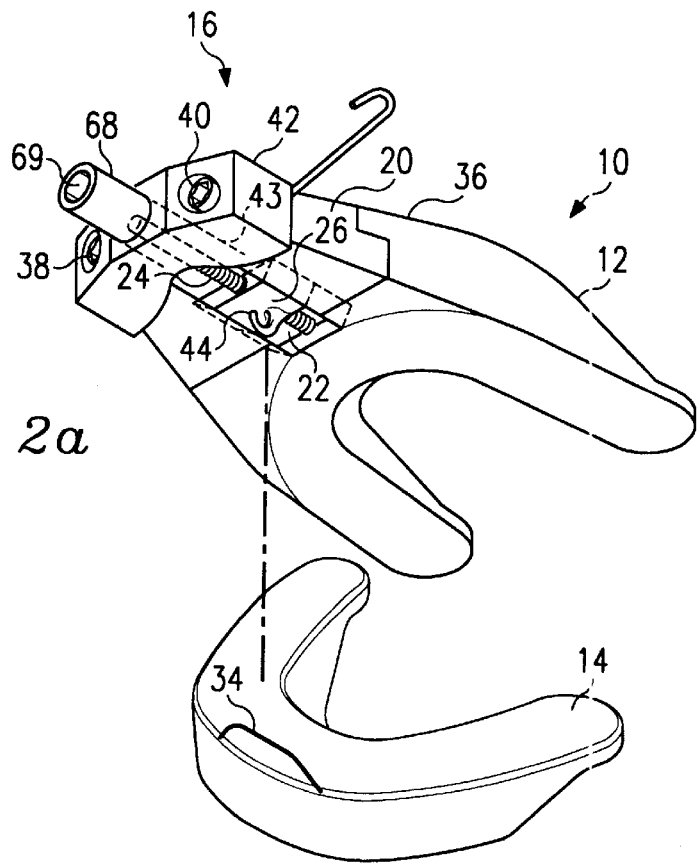

Alternatively, as shown in FIGURE 1b, arches 12 and 14 may themselves be formed from a deformable material that is suitable for dental uses, such as methylmethacrylate or a polycarbonate resin thermoplastic such as that sold under the name LEXAN. Such materials are known to those skilled in the art, and other appropriate materials may be used without departing from the intended scope of the present invention. Various securing clasps may be used to more fully secure upper arches 12 and 14 to the user's teeth. Illustrative embodiments include C-clasps 13, ball clasps 15, and U-clasps 17. Arches 12 and 14 may include any suitable securing in any suitable number.

Upper arch 12 is coupled to the remainder of device 10 using connector 16. In one embodiment, the body 20 of connector 16 is removably coupled to upper arch 12 using screws 18 and 19, although other fastening agents may be employed without departing from the intended scope of the present invention. The present invention contemplates an integral piece of material to form both body 20 and upper arch 12. Since body 20 of connector 16 is removable from upper arch 12, a mold of the user's upper teeth may be formed before device 10 is assembled and inserted into the user's mouth, providing an important technical advantage. Similarly, lower arch 14 is removably coupled to connector 16. As a result, device 10 may be customized by the user or a clinical professional without involving the remainder of device 10.

Connector 16 may provide a lip bumper 36 that allows the user's lips to form a seal around body 20. Lip bumper 36 reduces fatigue that may result from a user's tendency to form his or her lips tightly around an object whose cross-section is smaller than the opening formed by the user's lips when they are in a relaxed state. Lip bumper 36 also provides a more effective seal between the user's lips and body 20 to increase the effectiveness of CPAP system 88 discussed more fully below. Lip bumper 36 may be integral to or separate from connector 16. Alternatively, upper arch 12 may provide lip bumper 36 as appropriate, for example, according to the location of the coupling between upper arch 12 and connector 16. In this case, lip bumper 36 may be integral to or separate from upper arch 12. Body 20 is coupled to face plate 42 using screws 38 and 40 or any other suitable fastening agents. The present invention contemplates an integral piece of material forming both body 20 and face plate 42.

Device 10 may be adapted for use in connection with a face mask 86 and a continuous positive air pressure (CPAP) system 88 for supplying a gas to face mask 86. Face mask 86 may be configured so as to allow CPAP system 88 to supply gas at constant positive air pressure, at positive air pressure adjusted according to the particular user or breathing disorder being treated, or any other appropriate air pressure. Increasing the air pressure from CPAP system 88 generally increases the opening of the user's breathing passageway. CPAP system 88 is shown as an example only. Other systems for delivering any breathable gas, such as air, oxygen, or gases used in anaesthesia, at constant or varying pressures, may also be used. Face mask 86 is be configured to allow exhaled gas exhaled to be exhausted in a suitable manner from face mask 86.

In one embodiment, device 10 may include an adjustable strap 62 operable to engage strap hooks 64 and 66 coupled to face plate 42 of connector 16 to secure device 10 to the user's head. This allows device 10 to extend the user's lower jaw forward with less stress being placed on the user's upper jaw and therefore less risk of injury to the user's teeth. Adjustable strap 62 may also increase the effectiveness of CPAP system 88 in delivering gas to face mask 86. Adjustable strap 62 may engage one or both strap hooks 64 and 66, may attach only to face mask 86 or to a portion of connector 16, or may be configured in any other appropriate manner.

Face mask 86 is adjustably coupled to connector 16 and therefore to upper arch 12 using connecting apparatus 67, which includes a hollow post 68 that extends forward from face plate 42. Hollow post 68 meets and engages swivel collar 70, forming an adjustable collar joint through which hollow post 68 may slide and rotate. Fastener 72 couples swivel collars 70 and 74 at any desired angle relative to one another. Connecting post 76 extends at one end through swivel collar 74, forming a second adjustable collar joint through which connecting post 76 may slide and rotate. When fastener 72 is sufficiently tightened, the two collar joints formed by collars 70 and 74 with hollow post 68 and connecting post 76, respectively, are tightened.

Connecting post 76 may extend at the other end through collar 78, forming a third adjustable collar joint through which connecting post 76 may slide and rotate. Fastener 80 couples swivel collars 78 and 82 at any desired angle relative to one another. Post 84 may extend at its distal end through swivel collar 82, forming a fourth collar joint through which post 84 may slide and rotate. When fastener 80 is sufficiently tightened, the collar joints formed by swivel collars 78 and 82 with connecting post 76 and post 84, respectively, are tightened.

Post 84 may be secured to face mask 86 at its proximal end, completing the coupling of connector 16 to face mask 86. As a result, the present invention provides universal adjustability, allowing the portion of device 10 that is coupled to the user's mouth to be adjustably positioned forward, vertically, laterally, angularly, or rotationally with respect to face mask 86, which provides an important technical advantage. It should be understood that other methods of providing universal or lesser adjustability may be used with device 10 without departing from the intended scope of the present invention.

FIGS. 2a through 2d illustrate body 20 of connector 16 having a channel 22. Hooking element 26 is adapted to fit in channel 22 and to slide along the length of channel 22. Horizontal screw 24 extends from the front of body 20 rearward into channel 22 to engage hooking element 26. Screw head 25 of horizontal screw 24 may be accessed using horizontal hole 43 formed in face plate 42. A screwdriver or other suitable adjustment device may be inserted into horizontal hole 43 in face plate 42 to engage screw head 25. The hollow portion 69 of hollow post 68, which is coupled to connector 16 through face plate 42, provides access to horizontal hole 43 and screw head 25. Horizontal screw 24 may extend forward through face plate 42 and into hollow portion 69, may extend into horizontal hole 43 and not into hollow portion 69, or may rest within body 20 and not extend into horizontal hole 43.

In one embodiment, at least some portion of the side walls of channel 22 are formed diagonally so as to guide the travel of hooking element 26 forward or rearward within channel 22 when horizontal screw 24 is turned, while not allowing hooking element 26 to be displaced vertically to any substantial extent. Hooking element 26 slides forward or rearward within channel 22 in response to horizontal screw 24 being turned in the appropriate direction. The present invention contemplates side walls of channel 22 formed in any manner suitable to allow hooking element 26 to travel forward or rearward within channel 22, while not allowing hooking element 26 to be displaced vertically to any substantial extent.

Lower arch 14 includes hooking clasp 34, which extends laterally across the midline of lower arch 14 and engages hook 44. While engaged with hook 44, lower arch 14 may move laterally in response to lateral motions of the user's jaw, providing an important technical advantage. Hook 44 may be integral to or separate from hooking element 26. Although hooking clasp 34 is shown having a substantially circular cross-section, hooking clasp may have any suitable configuration. The present invention contemplates coupling hooking element 26 and hooking clasp 34 in any appropriate manner.

Due to the relative positions of hook 44 and hooking clasp 34, when hook 44 has engaged hooking clasp 34, lower arch 14 and thus the user's lower jaw may be extended forward, relative to upper arch 12. When horizontal screw 24 is turned in the appropriate direction, lower arch 14 and thus the user's lower jaw may be adjusted forward or rearward relative to upper arch 12 to according to the user and the breathing disorder being treated. Alternatively, hooking element 26 may be allowed to move freely through channel 22 unless a vertical screw or other suitable member is adjusted to apply a force sufficient to press hooking element 26 against the inner surface of channel 22 and secure hooking element 26 in the desired position. Hooking element 26 may be further adjusted by reducing or releasing the force pressing hooking element 26 against channel 22, moving hooking element 26 to the desired position, and then reapplying the force to hooking element 26. The present invention contemplates adjustably positioning the user's lower jaw using a motor or hydraulics, in connection with horizontal screw 24 or otherwise.

Figure 3A:
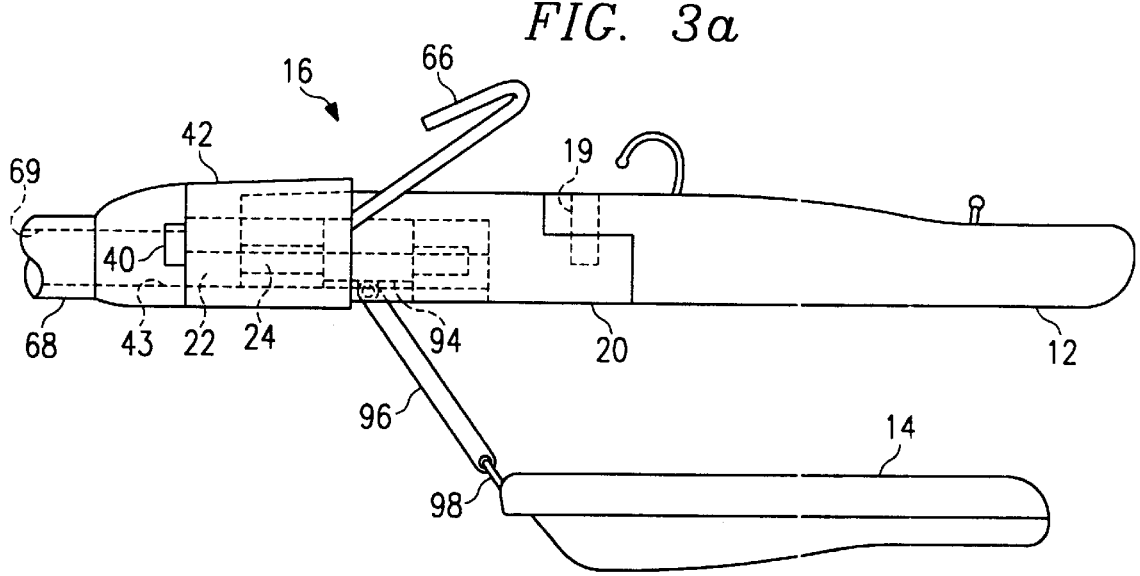
FIGS. 3a and 3b illustrate an alternative device for improving breathing that includes a slider.
Figure 3B:
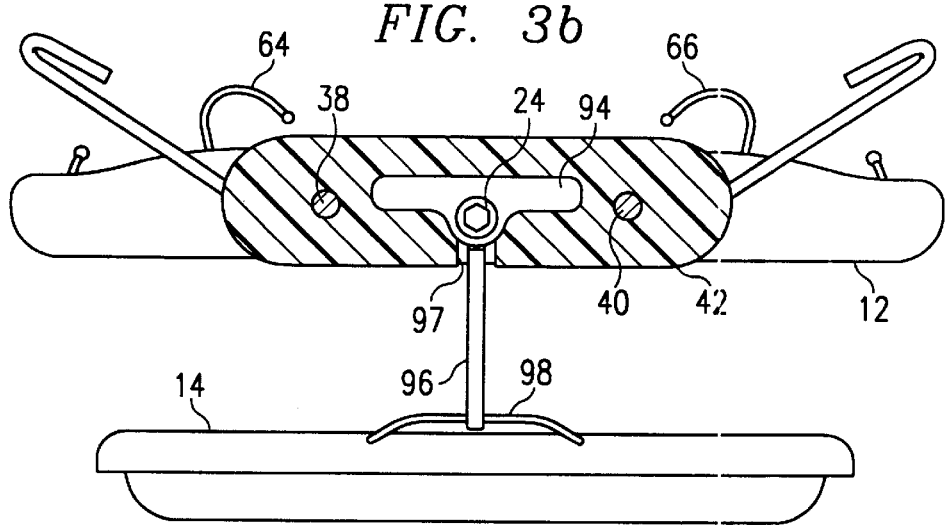

FIGS. 3a and 3b illustrate a device for improving breathing that includes a slider 94. Slider 94 is adapted to slide along the length of channel 22. Horizontal screw 24 extends from the front of body 20 rearward into channel 22 to engage slider 94. Screw head 25 of horizontal screw 24 may be accessed and adjusted as described above with reference to FIGS. 2a through 2d. In one embodiment, at least a portion of the side walls of channel 22 cooperate with slider 94 to guide slider 94 forward or rearward within channel 22 when horizontal screw 24 is turned in the appropriate direction, while not allowing slider 94 to be displaced vertically to any substantial extent.

Connecting arm 96 is coupled to slider 94 and extends generally downward from slider 94, through a slot 97 of channel 22, to a region generally below upper arch 12. Lower arch 14 includes lateral bar 98 operable to engage connecting arm 96 at its distal end. While engaged with connecting arm 96, lower arch 14 may move laterally in response to lateral motions of the user's lower jaw, which provides an important technical advantage. Connecting arm 96 may be integral to or separate from slider 94 and connecting arm 96 may be of variable length. Although lateral bar 98 is shown having a substantially circular cross-section, the present invention contemplates lateral bar 98 having any suitable configuration and coupling to connecting arm 96 in any suitable manner. Due to the relative positions of connecting arm 96 and lateral bar 98, when connecting arm 96 has engaged lateral bar 98, lower arch 14 and thus the user's lower jaw may be extended forward relative to upper arch 12 as discussed above with reference to FIGS. 2a through 2d.

FIGS. 4a through 4c illustrate an alternative device 10 for improving breathing that includes an alternative hooking element 26. Hooking element 26 is vertically as well as forwardly adjustable, allowing hooking element 26 to be raised or lowered as necessary to customize device 10 according to particular needs. As shown in FIGS. 4b and 4c, vertical screw 30 extends downward from the exposed upper portion 23 of channel 22 through a threaded hole in the top of hooking element 26 until vertical screw 30 contacts flange 28, which is separate from hooking element 26. Vertical screw 30 may travel forward or rearward within exposed upper portion 23 of channel 22 when hooking element 26 and flange 28 slide within channel 22 in response to horizontal screw 24 being adjusted. Being exposed from the top, vertical screw 30 is operable to adjust the vertical displacement of hooking element 26 from flange 28.

In one embodiment, vertical screw 30 is a set screw. Since flange 28 is prevented from moving vertically due to the shape of the side walls of channel 22, turning vertical screw 30 causes hooking element 26 to displace vertically relative to upper arch 12. A removable cap 32 may cover exposed upper portion 23 of channel 22 when vertical screw 30 is not being adjusted. Due to the complimentary shapes of channel 22, hooking element 26, flange 28, and vertical screw 30, hooking element 26 may be adjusted forwardly, rearwardly, and vertically, which provides an important technical advantage and increases the ease, effectiveness, and comfort of device 10 in improving breathing. Hooking element 26 may also be adjusted using a motor, hydraulics, or in any other suitable manner.

FIGS. 5a through 5d illustrate alternative devices 10 for improving breathing. As shown in FIG. 5a, the vertical length of hooking element 26 may be variable, such that the vertical distance between lower arch 14 and upper arch 12 may be increased. Hooking element 26 is adjustable forwardly, rearwardly, and vertically, as discussed above. As shown in FIG. 5b, hook 44 may be fixedly or removably attached to hooking element 26, may be glued or otherwise coupled to hooking element 26, may be insertionally glued or force fitted into a hole drilled in hooking element 26, may be screwed into hooking element 26, or may be attached in any other manner to hooking element 26. As shown in FIG. 5c, the vertical length of hook 44 is also variable, such that any suitable combination of hook 44 and hooking element 26 may be used to achieve vertical displacement of lower arch 14 relative to upper arch 12.

FIG. 5d illustrates an alternative embodiment of hook 44 that includes a flexible member 46, such as a spring or rubberband, disposed between connector 16 and hook 44. When hook 44 has engaged hooking clasp 34 of lower arch 14 to extend the user's lower jaw forward, the jaw may still enjoy at least some freedom of movement due to flexible member 46. Not only does this configuration enable the user to be more comfortable when using device 10, flexible member 46 reduces any risk that the user's teeth may be injured as a result of quick and forceful movements of the user's lower jaw. Flexible member 46 may be incorporated into any of the embodiments described above or into any combination thereof, whether or not shown or described. In another embodiment, flexible member 46 is fixedly or removably attached to connector 16 at one end and fixedly or removably attached to lower arch 14 at the other end, coupling connector 16 to lower arch 12 directly. Other mechanisms designed to dampen the force transferred to and between upper arch 12 and lower arch 14 may be used without departing from the intended scope of the present invention.

Figure 6A:
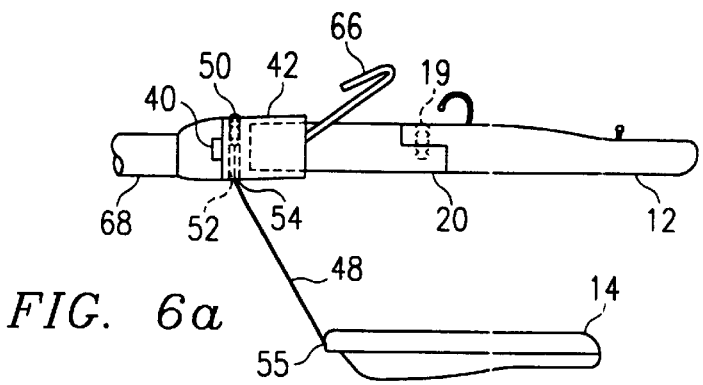
FIGS. 6a through 6c illustrate another alternative device for improving breathing.
Figure 6B:
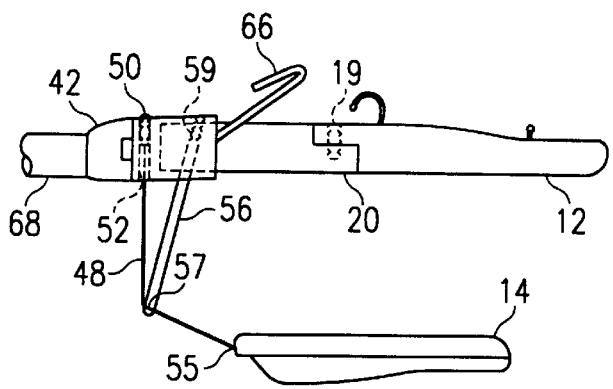
Figure 6C:
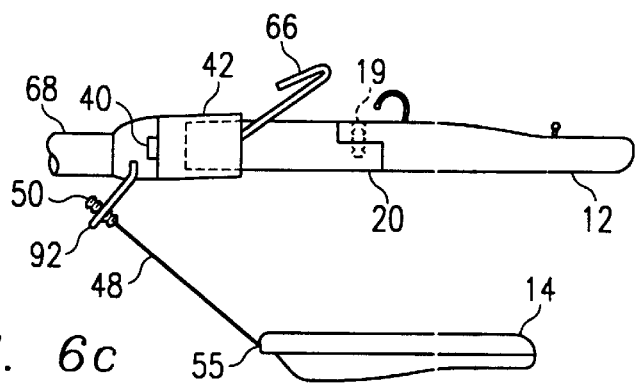

FIGS. 6a through 6c illustrate a device 10 for improving breathing that includes tensile member 48 under tension, for example, a monofilament line. Tensile member 48 may be constructed in any shape and from any material suitable to extend the user's lower jaw forward when tensile member 48 is placed under tension. As shown in FIGS. 6a and 6b, tensile member 48 is secured to tension screw 50 at the generally top and forward surface of face plate 42 of connector 16. Tension screw 50 is operable to displace tensile member 48 in response to adjustment of tension screw 50. From its attachment at tension screw 50, tensile member 48 extends generally downward through hole 52, contacts support surface 54 as it leaves hole 52 at the generally bottom surface of face plate 42, and extends to attachment point 55 on lower arch 14. Attachment point 55 may be at any suitable location on lower arch 14. When tension screw 50 is adjusted, lower arch 14 is pulled in the direction of tensile member 48 to extend the user's lower jaw is forward relative to upper arch 12.

The present invention contemplates other appropriate configurations of tension screw 50, hole 52, and support surface 54 to pull lower arch 14 generally forward in the direction of tensile member 48 when tension screw 50 is adjusted. In one embodiment, tensile member 48 is allowed to move freely through hole 52 unless a screw or other suitable member is adjusted to press tensile member 48 within hole 52 against the inner surface of hole 52 with a force sufficient to secure tensile member 48 in the desired position. Tensile member 48 may be further adjusted by reducing or releasing the force pressing tensile member 48 against the inner surface of hole 52, moving tensile member 48 to the desired position, and then reapplying the force to tensile member 48. The present invention contemplates adjusting tensile member 48 using a motor or hydraulics to adjustably position the user's lower jaw.

Device 10 allows the user's lower jaw to be adjustably positioned forwardly in response to tension directed from a point forward relative to the user's lower jaw. The upward vertical component of the tension on lower arch 14 is decreased the more nearly horizontal the direction of tension placed on lower arch 14 using tensile member 48. As the upward vertical component of the tension decreases, so does the possibility that lower arch 14 will be pulled off the user's lower teeth when the mouth is opened or the lower jaw is moved. It is therefore desirable to direct the tension on lower arch 14 from a point forward of lower arch 14 and below attachment point 55 of tensile member 48 or nearly horizontal with attachment point 55.

Hole 52 may be formed so as to cause tensile member 48 to contact the inner surface of hole 52 at support surface 54 before extending to attachment point 55. In this case, tensile member 48 is redirected such that the angle of its attachment to lower arch 14, relative to the horizontal, is more acute than it would be if tensile member 48 extended in a straight line between tension screw 50 and attachment point 55. This reduces the vertical component of tension on lower arch 14. The positions and angles of hole 52 and support surface 54 may be varied to adjust the angle at which tensile member 48 attaches to lower arch 14, thereby adjusting the vertical component of the tension on lower arch 14 as appropriate.

Since reducing the upward vertical component of the tension on lower arch 14 reduces the possibility that lower arch 14 will be pulled off the user's lower teeth when the mouth is opened or the lower jaw is moved, it is desirable to locate support arm surface 57 near the end of support arm 56, which extends generally downward from connector 16 to a point generally forward of lower arch 14. Tensile member 48 contacts and is redirected by support arm surface 57, support surface 54, or both support arm surface 57 and support surface 54. Support arm surface 57 is positioned vertically to allow tensile member 48 to exert a tensile force on lower arch 14 in a generally horizontal direction when tension screw 50 is appropriately adjusted, providing benefits discussed above.

Support arm 56 may be integral to or separate from connector 16, may be fixedly coupled to connector 16, or may be coupled to connector 16 in a manner that allows support arm 56 to be extended or retracted as extension screw 59 is suitably adjusted. Variations in the manner of attachment of support arm 56 to device 10 and in the adjustability of support arm 56 are within the intended scope of the present invention. Support arm 56 may include a hole in its distal end that provides support arm surface 57, support arm 56 may have a bifurcated end to constrain tensile member 48 laterally as it contacts and travels over support arm surface 57, or a pulley 58 mounted on the end of support arm 56 may provide support arm surface 57. Any appropriate configuration of support arm surface 57 and support arm 56 may be used to reduce the upward vertical component of tension on lower arch 14.

FIG. 6c illustrates device 10 in which the point at which tensile member 48 couples to connector 16 is below face plate 42. A mount 92 projects generally downward from connector 16 and adjustably couples tension screw 50, which couples to tensile member 48, to connector 16. As before, tensile member 48 is secured to lower arch 14 at attachment point 55, allowing lower arch 14 to be adjusted forwardly when tension screw 50 is turned. The location and vertical length of mount 92 may be varied as necessary to properly size device 10 to the user and to effectively treat the breathing disorder involved. The upward vertical component of the tension placed on lower arch 14 may be reduced or eliminated if device 10 is configured such that attachment point 55 is nearly level with or above the coupling of tensile member 48 to mount 92.

Figure 7:
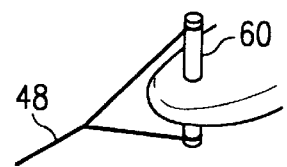
FIG. 7 illustrates a device for improving breathing that includes a tongue stud.

FIG. 7 illustrates device 10 that includes a tongue stud 60 that pierces the user's tongue and is then secured to the remainder of device 10. Tongue stud 60 may be used in connection with any or all of the embodiments of the present invention described above to replace or combine with the functions of lower arch 14. For example, tongue stud 60 may be coupled to tensile member 48 in any of the embodiments illustrated in FIGS. 6a through 6c. If used in connection with tensile member 48, tongue stud 60 may extend the user's tongue forward when tension is placed on tensile member 48 to improve the breathing of the user. Although tongue stud 60 is described in connection with tensile member 48, tongue stud 60 may be coupled to hook 44, hooking element 26, connecting arm 96, slider 94, or any other portion of connector 16 in any or all of the embodiments discussed above. The present invention further contemplates alternate embodiments wherein tongue stud 60 is positioned using a motor or hydraulics.

Figure 8:
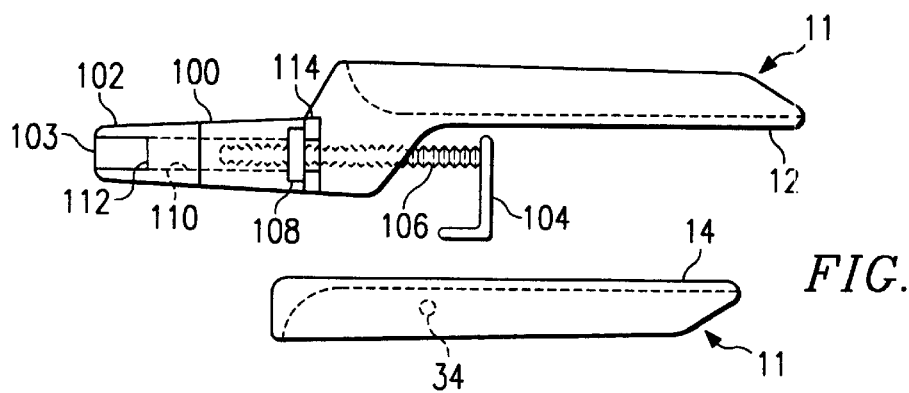
FIG. 8 illustrates an exemplary device for improving breathing according to the present invention.

FIG. 8 illustrates an exemplary device 10 having an adjustor 100 that is integral to or separate from upper arch 12. Adjustor 100 includes a cylindrical or other suitable channel 110 that extends from front wall 114 of upper arch 12 through adjustor 100 to front 103 of rotating portion 102 of adjustor 100. Engager 112 includes a shaft disposed within channel 110 and an internally threaded head 108 that may rotate within adjustor 100 while engaged with threads on shaft 106 of hook 104. Engager 112 is fixedly coupled to rotating portion 102 of adjustor 100, such that when rotating portion 102 is rotated, engager 112 and head 108 of engager 112 are likewise rotated within channel 110. Although engager 112 is shown as accessible from front 103 of rotating portion 102 through a portion of channel 110, the present invention contemplates rotating portion 102 completely isolating the forward portion of engager 112, rotating portion 102 being integral to engager 112, or rotating portion 102 and engager 112 in any other suitable configuration.

Although rotating portion 102 and engager 112 may be formed from any suitable material, in one embodiment engager 112 is formed from stainless steel or another relatively inert metal and rotating portion 102 is formed form the material that forms upper arch 12.

In operation, arches 12 and 14 are inserted into the user's mouth, either separately or together, and hook 104 removably engages hooking clasp 34 of lower arch 14, which extends between opposite sides of lower arch 14. When rotating portion 102 of adjustor 100 is rotated in an appropriate direction, internal threads of head 108 of engager 112, which are engaged with threads of shaft 106, rotate to adjust hook 104 forwardly relative to upper arch 12. This adjusts lower arch 14 forwardly relative to upper arch 12 and extends the user's lower jaw forwardly relative to upper arch 12 to reduce or eliminate snoring, obstructive sleep apnea, or other breathing disorders. Although forwardly adjusting lower arch 14 and the user's lower jaw is discussed, device 10 operates similarly to adjust lower arch 14 and the user's jaw rearwardly relative to upper arch 12.

FIGS. 9a through 9c illustrate upper arch 12 and lower arch 14 of device 10. As shown in FIG. 9a, in which upper arch 12 is shown from below, connector 120 may be removably coupled to adjustor 100 of upper arch 12 to allow upper arch 12 to be removably coupled to face mask 86 or other suitable face mask. In one embodiment, at least a portion of adjustor 100, for example, some or all of rotating portion 102, is pressure fitted into cavity 122 of connector 120. Shaft 124 of connector 120 may then be coupled to face mask 86 using appropriate portions of connecting apparatus 67 discussed above with reference to FIG. 1. In this situation, shaft 124 replaces or combines with the function of hollow post 68.

In one embodiment, shaft 106 of hook 104 is substantially flattened, as discussed more fully below with reference to FIG. 10. In this case, only the rounded sides of shaft 106 are threaded and engage internal threads of head 108 of engager 112. As shown in exploded FIG. 9b, hook 104 includes indices 126 that cooperate with zero set 128 to indicate the extent of forward or rearward adjustment of hook 104 relative to upper arch 12, which in turn indicates the extent of adjustment of lower arch 14 and the user's lower jaw. Although indices 126 and zero set 128 are discussed, the present invention contemplates any suitable technique for indicating the extent to which the user's lower jaw is adjusted.

As shown in FIG. 9c, hooking clasp 34 may be any suitable rod or similar member that extends between opposite sides of lower arch 14. Hooking clasp 34 may be substantially circular in cross section or may have any other suitable configuration. Although hooking clasp 34 is shown as substantially linear, the present invention contemplates any hooking clasp 34 suitable to removably engage hook 104 to allow lower arch 14 to be adjusted forwardly relative to upper arch 12 in the manner discussed above. When hook 104 is engaged with hooking clasp 34, lower arch 14 is allowed to move laterally relative to upper arch 12, providing increased comfort to the user and improved treatment.

FIG. 10 illustrates front wall 114 of upper arch 12, shown from the rear of upper arch 12, that separates adjustor 100 from upper arch 12. Wall 114 includes a horizontal slot 116 through which shaft 106 of hook 104 extends into internally threaded head 108 of engager 112. In one embodiment, as discussed above, shaft 106 of hook 104 is flattened, such that slot 116 limits or prevents rotation of shaft 106 when rotating portion 102 of adjustor 100 is rotated to rotate internally threaded head 108 of engager 112. As a result, hook 104 is adjusted forwardly relative to upper arch 12 in response to rotation of head 108, for example, in the direction of arrow 118. The present invention contemplates features or operation of device 10 discussed with reference to FIGS. 8 through 10 replacing or combining with features or operation of devices 10 discussed with reference to FIGS. 1 through 7. Although front wall 114 is discussed, if adjustor 100 is integral to upper arch 12, slot 116 may be formed within this integral piece of material or a component secured within this integral piece of material. Front wall 114 may be a stainless steel or other metal component that is separate from both upper arch 12 and adjustor 100.

Although the present invention has been described above in connection with several embodiments, it should be understood that a plethora of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A device for improving the breathing of a user, comprising:

an upper arch adapted to receive at least some of the user's upper teeth;

a lower arch adapted to receive at least some of the user's lower teeth; and a hook coupled to the upper arch and uncoupled from the lower arch until the device is inserted into the user's mouth, the hook operable to removably engage the lower arch after the device has been inserted into the user's mouth to adjustably position the lower arch forwardly relative to the upper arch.

2. The device of claim 1, wherein at least one of the upper and lower arches comprises a deformable material operable to form a mold of at least some of the user's teeth.

3. The device of claim 1, wherein the lower arch is operable to move laterally relative to the upper arch in response to lateral motion of the user's jaw.

4. The device of claim 1, wherein the upper arch further comprises an adjustor operable to rotate to adjust the hook forwardly relative to the upper arch.

5. The device of claim 4, wherein the upper arch further comprises a slot, at least a portion of the hook passing through the slot, the slot operable to limit the rotation of the hook.

6. The device of claim 4, wherein the adjustor comprises an internally threaded channel operable to engage threads of the hook.

7. The device of claim 1, wherein the lower arch comprises a hooking clasp extending laterally between opposite sides of the lower arch, the hook engaging the hooking clasp to engage the lower arch.

8. The device of claim 1, further comprising a removable connector operable to couple the device to a face mask.

9. The device of claim 1, wherein the hook comprises indices operable to indicate the forward adjustment of the lower arch relative to the upper arch.

10. A device for improving the breathing of a user, comprising:

an upper arch adapted to receive at least some of the user's upper teeth;

a lower arch adapted to receive at least some of the user's lower teeth;

a hook coupled to the upper arch and operable to removably engage the lower arch; and an adjustor operable to adjust the hook while the device is in the user's mouth to adjustably position the lower arch forwardly relative to the upper arch.

11. The device of claim 10, wherein the adjustor is operable to rotate to adjust the hook forwardly relative to the upper arch.

12. The device of claim 10, wherein the lower arch comprises a hooking clasp extending laterally between opposite sides of the lower arch, the hook engaging the hooking clasp to engage the lower arch.

13. A method of improving the breathing of a user, comprising:

inserting an upper arch into the user's mouth, the upper arch being coupled to a hook and adapted to receive at least some of the user's upper teeth;

inserting a lower arch into the user's mouth, the lower arch being adapted to receive at least some of the user's lower teeth;

removably engaging the lower arch with the hook; and adjusting the hook while the upper and lower arches are in the user's mouth to adjustably position the lower arch relative to the upper arch.

14. The method of claim 13, further comprising the step of forming a mold of at least some of the user's teeth using a deformable material of at least one of the upper and lower arches.

15. The method of claim 13, further comprising the step of allowing the lower arch to move laterally relative to the upper arch in response to lateral motion of the user's jaw.

16. The method of claim 13, further comprising the step of rotating an adjustor coupled to the upper arch to adjust the hook forwardly relative to the upper arch.

17. The method of claim 16, further comprising the step of engaging threads of the hook using an internally threaded shaft of the adjustor.

18. The method of claim 13, wherein the step of engaging the lower arch comprises the step of engaging a hooking clasp extending laterally between opposite sides of the lower arch.

19. The method of claim 13, further comprising the step of removably coupling a connector to the upper arch, the connector operable to couple the upper arch to a face mask.

20. The device of claim 13, further comprising the step of indicating the forward adjustment of the lower arch relative to the upper arch using indices associated with the hook.

\* \* \* \* \*

UNITED STATES PATENT AND TRADEMARK OFFICE
CERTIFICATE OF CORRECTION

PATENT NO.     : 5,954,048
DATED          : September 21, 1999
INVENTOR(S)    : W. Keith Thornton It is certified that error appears in the above-identified patent and that said Letters Patent is hereby corrected as shown below:

Column 12,
Line 55, after "The", delete "device" and insert -- method --.

Signed and Sealed this

Twenty-first Day of October, 2003

JAMES E. ROGAN
*Director of the United States Patent and Trademark Office*